US012788975B2

(12) United States Patent
Housley et al.

(10) Patent No.: US 12,788,975 B2
(45) Date of Patent: Nov. 10, 2026

(54) METHOD AND SYSTEM FOR CONTROLLING MOLECULAR ELECTROTRANSFER

(71) Applicant: NEWSOUTH INNOVATIONS PTY LIMITED, Sydney (AU)

(72) Inventors: Gary David Housley, Sydney (AU); Jeremy Pinyon, Sydney (AU); Nigel Hamilton Lovell, Sydney (AU); Amr Al Abed, Sydney (AU)

(73) Assignee: NEWSOUTH INNOVATIONS PTY LIMITED, Sydney (AU)

(*) Notice: Subject to any disclaimer, the term of this patent is extended or adjusted under 35 U.S.C. 154(b) by 937 days.

(21) Appl. No.: 17/413,412

(22) PCT Filed: Dec. 13, 2019

(86) PCT No.: PCT/AU2019/051381
§ 371 (c)(1),
(2) Date: Jun. 11, 2021

(87) PCT Pub. No.: WO2020/118383
PCT Pub. Date: Jun. 18, 2020

(65) Prior Publication Data

US 2022/0054827 A1 Feb. 24, 2022

(30) Foreign Application Priority Data

Dec. 13, 2018 (AU) ................................ 2018904743

(51) Int. Cl.
*A61N 1/32* (2006.01)
*A61N 1/05* (2006.01)

(52) U.S. Cl.
CPC ............... *A61N 1/327* (2013.01); *A61N 1/05* (2013.01)

(58) Field of Classification Search
CPC ........ A61N 1/327; A61N 1/05; A61N 1/0412; A61N 1/05829; A61N 1/18; A61N 1/00;
(Continued)

(56) References Cited

U.S. PATENT DOCUMENTS 6,055,453 A 4/2000 Hofmann et al.
6,241,701 B1 * 6/2001 Hofmann .............. A61N 1/325 607/116

(Continued)

FOREIGN PATENT DOCUMENTS

CN 1658924 A 8/2005
JP 2005-523085 A 8/2005

(Continued)

*Primary Examiner* — Kevin C Sirmons
*Assistant Examiner* — Antarius S Daniel
(74) *Attorney, Agent, or Firm* — Finnegan, Henderson, Farabow, Garrett & Dunner, LLP

(57) ABSTRACT

A method for controlling electrotransfer delivery of therapeutic molecules to targeted groups of cells uses a system including an array of two or more physically contiguous electrodes inserted into biological tissue and a pulse generator selectively driving the electrodes as one or more anodes and one or more cathodes for application of one or more electrical pulses. The method includes determining first and second selections of the electrodes to drive as anodes and as cathodes using one or more electric pulses; determining parameters for the electric pulses to generate first and second shaped electric fields for a target treatment region adjacent the array; determining a waiting period duration between generating the first electric field and generating the second electric field; applying a first sequence of unipolar pulses using the first selection of electrodes; after the waiting period, applying a second sequence of unipolar pulses using the second selection of electrodes.

19 Claims, 13 Drawing Sheets

(58) Field of Classification Search
CPC ...... A61N 1/04; A61N 1/0416; A61N 1/0502; A61N 1/40
See application file for complete search history.

(56) References Cited

U.S. PATENT DOCUMENTS

| | | | | |
|---|---|---|---|---|
| 9,987,081 | B1 * | 6/2018 | Bowers | A61B 18/1492 |
| 2006/0089674 | A1 | 4/2006 | Walters et al. | |
| 2010/0210994 | A1 * | 8/2010 | Zarif | A61N 1/0416<br>604/20 |
| 2016/0129246 | A1 | 5/2016 | Housley et al. | |

FOREIGN PATENT DOCUMENTS

| | | | | | |
|---|---|---|---|---|---|
| WO | WO 00/45823 | A1 | | 8/2000 | |
| WO | WO 03/013615 | A1 | | 2/2003 | |
| WO | WO 03/089046 | A1 | | 10/2005 | |
| WO | WO-2016205895 | A1 | * | 12/2016 | A61B 18/00 |

* cited by examiner

METHOD AND SYSTEM FOR CONTROLLING MOLECULAR ELECTROTRANSFER

CROSS-REFERENCE TO RELATED APPLICATIONS

This application is a national stage of International Application No. PCT/AU2019/051381, filed Dec. 13, 2019, and is based upon and claims the benefit of priority from Australian Patent Application No. 2018904743, filed Dec. 13, 2018, the entire contents of which are incorporated herein by reference.

TECHNICAL FIELD

The present invention relates to a system for electrotransfer delivery (also referred to as electroporation) of therapeutic molecules such as naked plasmid DNA or RNA to targeted groups of cells within tissues. Examples of applications of the system are for delivery of DNA to cells using a close field electrotransfer (electroporation) system using arrays of contiguous electrodes, where the electrodes are integrated within an array that is inserted into the tissue and cells targeted for electroporation are adjacent to, rather than between the electrodes.

BACKGROUND TO THE INVENTION

Electroporation is a technique used in molecular biology where an electrical field is applied to cells in order to increase the permeability of the cell membrane, thereby allowing chemicals, drugs, DNA or RNA to be introduced into the cell. The underlying principle is that an electric field generated by a high voltage pulse between two electrodes causes a transient dielectric breakdown of the plasma membrane of cells within the high intensity electric field, enabling DNA or other molecules to enter the cells.

Conventional electroporation uses electric fields between physically separated electrodes resulting in a direct current path through tissue between the electrodes. The inventors discovered that utilising an electric field adjacent a physically contiguous linear electrode array could achieve transfection of cells in the vicinity of the array using lower cumulative charge than required to achieve transfection of the same number of cells using open field electroporation, where target cells or tissue are placed in a direct current path between electrodes. Development of techniques for stimulating transfection within a target area adjacent a contiguous electrode array, is described in the inventors' previous patent applications, publication nos. WO2011/006204, WO2014/201511 and WO2016/205895 the disclosure of which provides background to the present disclosure, and may be referred to for a better understanding of the inventors' close field electroporation techniques. In WO2016/205895 the inventors disclose a system where the area within which electronically stimulated cell transfection occurs is controlled by controlling gradients within the generated electric field based on the electrode array configuration and pulse sequence applied to generate the electric field. The system of WO2016/205895 illustrates a practical application of the discovery, by the inventors, of improved cell transfection within an area of tissue subject to steeper electric field gradients. The invention applies this discovery to targeting regions for cell transfection adjacent the array by configuring the electrode array geometry and pulse sequence to drive the array to control the shape of the electric field to generate contours in the electric field through the target region. The variables for controlling the electric field shape include the physically contiguous electrode array configuration and stimulation pulse parameters. Using controlled electric filed shaping has enabled improved efficacy of cell transfection at lower cumulative charge than previously known open field electroporation. However, there is a desire to further improve electrotransfer techniques.

SUMMARY OF THE INVENTION

According to a first aspect there is provided a method of controlling electrotransfer delivery of therapeutic molecules to targeted groups of cells using a system comprising an array of two or more physically contiguous electrodes configured to be inserted into biological tissue and a pulse generator configured to selectively drive the two or more electrodes as one or more anodes and one or more cathodes for application of electrical pulses, the method comprising:

- determining a first selection of electrodes to drive as anodes and cathodes using one or more electric pulses, and for the selected electrodes determine electrical pulse parameters for the one or more electric pulses to generate a first shaped electric field for a target treatment region adjacent the array, wherein the physical configuration of the electrodes, selection of electrodes and anodes and cathodes, and applied electrical pulse parameters, control contours of gradients within the electric field for the target treatment region adjacent the array;
- determining a second selection of electrodes to drive as anodes and cathodes using one or more electric pulses, and for the selected electrodes determine electrical pulse parameters for the one or more electric pulses to generate a second shaped electric field for a target treatment region adjacent the array;
- controlling the pulse generator to apply a first sequence of one or more unipolar pulses using the first selection of electrodes driven as anodes and cathodes to generate a first shaped electric field; and
- controlling the pulse generator to apply a second sequence of one or more unipolar pulses using the second selection of electrodes driven as anodes and cathodes to provide a second shaped electric field.

According to another aspect there is provided an electrotransfer delivery system comprising:

- an array of two or more physically contiguous electrodes configured to be inserted into biological tissue;
- a pulse generator electrically connected to the electrodes of the array and configured to apply one or more electrical pulses to selectively drive the two or more electrodes as one or more anodes and one or more cathodes to generate an electric field in biological tissue adjacent the array, wherein the electric field is shaped to provide controlled contours of gradients within the electric field based on the physical configuration of the electrodes, selection of electrodes and anodes and cathodes, and applied electrical pulse parameters; and
- a controller configured to control the pulse generator, the controller being configured to control the pulse generator to apply a first sequence of one or more unipolar pulses using a first configuration of electrodes driven as anodes and cathodes to provide a first shaped electric field, and a second sequence of one or more unipolar pulses using a second configuration of electrodes driven as anodes and cathodes to provide a second shaped electric field.

In an embodiment of the system one or more further electrodes are selected to drive as anodes and cathodes using one or more electric pulses, and for the selected electrodes electrical pulse parameters are determined for the one or more electric pulses to generate a second shaped electric field for a target treatment region adjacent the array; and for each further selection of electrodes the controller controls the pulse generator to apply a further sequence of two or more unipolar pulses using each further selection of electrodes driven as anodes and cathodes to generate each further shaped electric field, wherein each further selection generates different controlled electric field gradients within the target treatment region to electric field gradients of a preceding electric field. A sequence of selections of electrodes and pulses can be chosen to generate a sequence of electric fields where subsequent electric fields each have electric field gradients through the target treatment region at an incremental angle relative to a preceding electric fields.

In an embodiment the first selection of electrodes comprises a linear configuration of one or more anodes and one or more cathodes, and the second selection of electrodes comprises the same electrode with anodes and cathodes switched to thereby reverse polarity.

In an embodiment the electrode array is a two-dimensional array and wherein the first selection of electrodes comprises a configuration of one or more anodes and one or more cathodes, and the second selection of electrodes comprises a configuration of electrodes including different electrodes from the first selection, selected to generate a change in electric field gradients within the target treatment region.

The method can further comprise the steps of determining one or more further selections of electrodes to drive as anodes and cathodes using one or more electric pulses, and for the selected electrodes determine electrical pulse parameters for the one or more electric pulses to generate a second shaped electric field for a target treatment region adjacent the array; and for each further selection of electrodes controlling the pulse generator to apply a further sequence of one or more unipolar pulses using each further selection of electrodes driven as anodes and cathodes to generate each further shaped electric field, wherein each further selection generates different controlled electric field gradients within the target treatment region to electric field gradients of a preceding electric field. In an embodiment a sequence of selections of electrodes and pulses are chosen to generate a sequence of electric fields where subsequent electric fields each have an electric field gradient through the target treatment region at an incremental angle relative to a preceding electric field.

In some embodiments increasing or decreasing spacing between anodes and cathodes is used to control the radius of the treatment area.

BRIEF DESCRIPTION OF THE DRAWINGS

An embodiment, incorporating all aspects of the invention, will now be described by way of example only with reference to the accompanying drawings in which.

DETAILED DESCRIPTION

Figure 1:
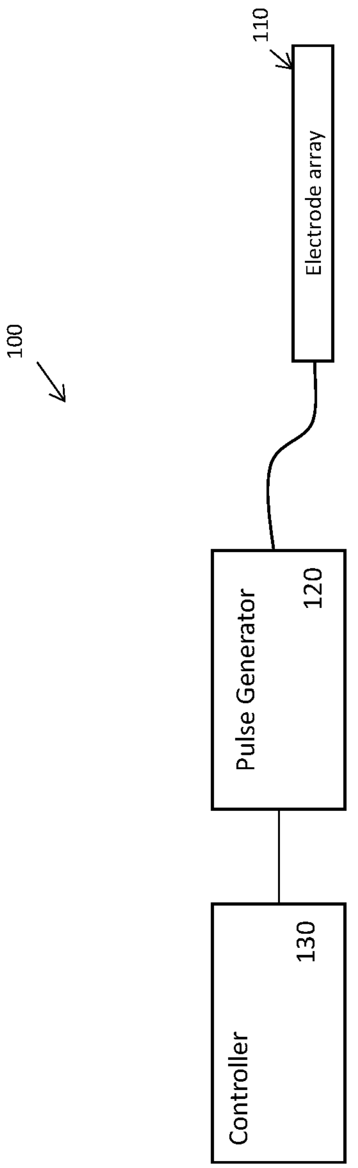
FIG. 1 is an exemplary block diagram of an electrotransfer system in accordance with an embodiment of the invention.

An electrotransfer system is disclosed which utilises changes in direction of electric field gradients to aid delivery of molecules, such as naked plasmid DNA, to cells. The system 100 (as illustrated in the block diagram of FIG. 1) includes an array 110 of two or more physically contiguous electrodes configured to be inserted into biological tissue, a pulse generator 120 and a controller 130. The pulse generator 120 is electrically connected to the electrodes of the array 110 and configured to apply one or more electrical pulses to selectively drive the two or more electrodes as one or more anodes and one or more cathodes to generate an electric field in biological tissue adjacent the array. The physical configuration of the electrodes, selection of electrodes and anodes and cathodes, and applied electrical pulse parameters control the shape and contours of gradients within the electric field generated in the tissue adjacent the electrode array. The controller 130 is configured to control the pulse generator 120 to apply a first sequence of one or more unipolar pulses using a first configuration of electrodes driven as anodes and cathodes to provide a first shaped electric field, and a second sequence of one or more unipolar pulses using a second configuration of electrodes driven as anodes and cathodes to provide a second shaped electric field. The effect achieved using the shaped electric fields and different first and second electric field gradients is increasing the amount of the surface area of cells where molecules may be stimulated by the electric field gradients to contact the cell and enter the cell via electrotransfer. Increasing the area of the cell membrane coated with molecules increases the likelihood of the cell taking up the molecule (transfection). Where only one pulse of each polarity is used electrotransfer efficiency is improved if there is a waiting period between the two different polarity pulses. In an embodiment the waiting period is 15 ms or longer, for example 15-400 ms, alternatively 10-600 ms. A waiting period may also be used between polarity changes where two (or more) sequences of two or more unipolar pulses are used.

The array 110 may be configured for temporary insertion into tissue, for example the array may be incorporated into a probe for insertion into tissue for treatment, then removed. The array may be configured as a linear array of electrodes. Alternatively, two or three dimensional arrays of contiguous electrodes may be used. The array may be configured to allow some for electrodes to drive as anodes and cathodes to be selected out of a larger number of electrodes (so not all are driven at once), this can enable varying configurations of anodes and cathodes based on the selection of electrodes and polarities. Alternatively, the array may be preconfigured as two electrodes (or a plurality of electrodes ganged together to operate as single electrodes) and selectively driven as anodes or cathodes. In some embodiments the array may be implantable, for example a cochlear implant array which may be configured for use in an electrotransfer mode in addition to an auditory stimulation mode, or bionic electrode arrays compatible with deep brain stimulation may similarly be developed with this dynamic electric field shaping modality for molecular electrotransfer. Other types of implantable arrays may be configured for implantation into a target region for an extended period to enable multiple applications of electrotransfer based therapy over time (for example weeks, months or years). All such variations are considered within the scope of the present disclosure.

Figure 2:
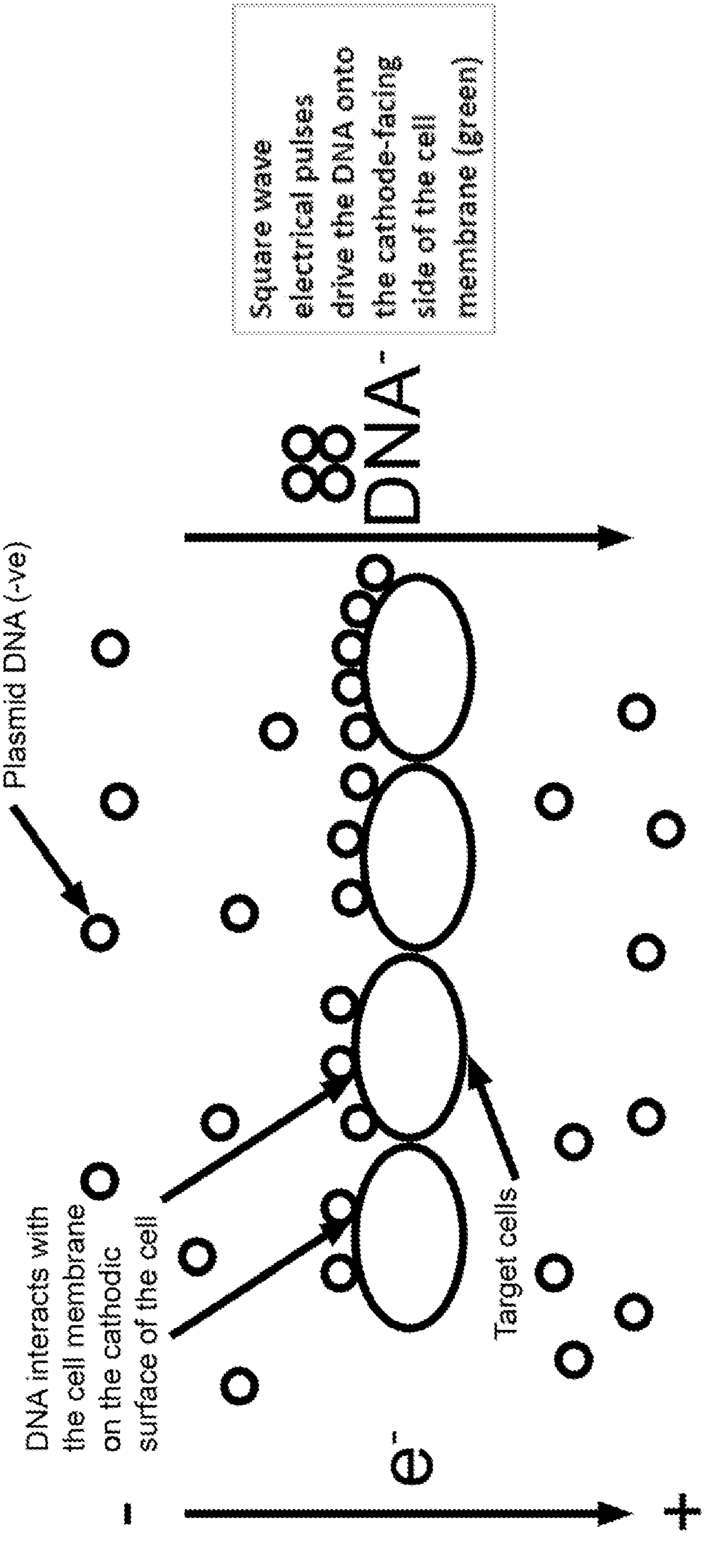
FIG. 2 illustrates polarised electrotransfer of DNA to cells.

It is known that the DNA electrotransfer to cells is polarized. When sufficient voltage is applied to generate an electric field suitable for delivery of naked DNA to cells, this DNA accumulates on the cathode-facing side of the cells (e.g. Electromediated formation of DNA complexes with cell membranes and its consequences for gene delivery as demonstrated in FIG. 2. The schematic shown in FIG. 2 illustrates the take up by cells DNA only entering the target cells from one side. To improve electrotransfer efficiency it is desirable to improve coverage of the cells by the DNA. Alternating polarity of electroporation pulses would therefore be expected to improve the efficacy of cell transfection—however work by the inventors has demonstrated that using alternating pulses in fact reduces transfection efficacy.

Figure 3:
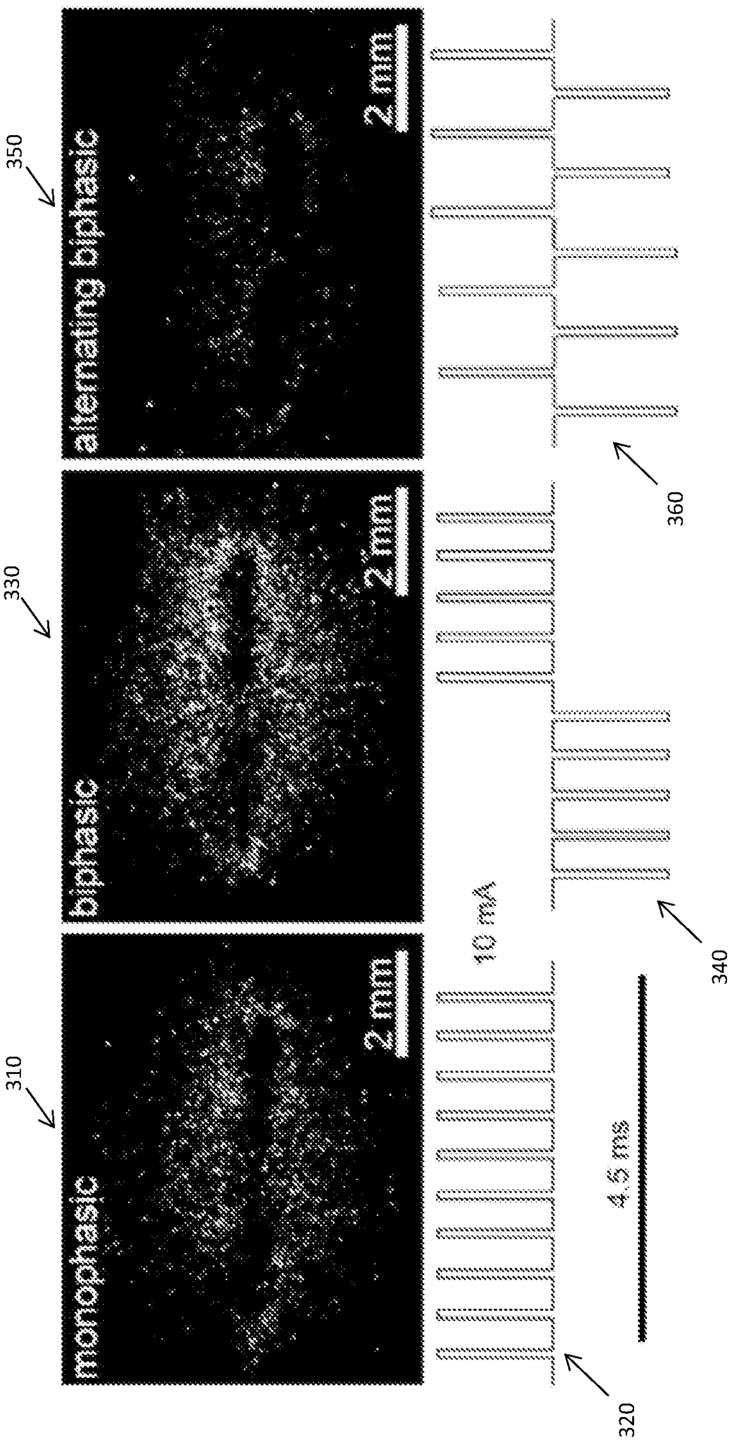
FIG. 3 illustrates expression of reporter plasmid DNA by HEK293 cells using the same 2-electrode linear array driven using different pulse sequences.
Figure 4:
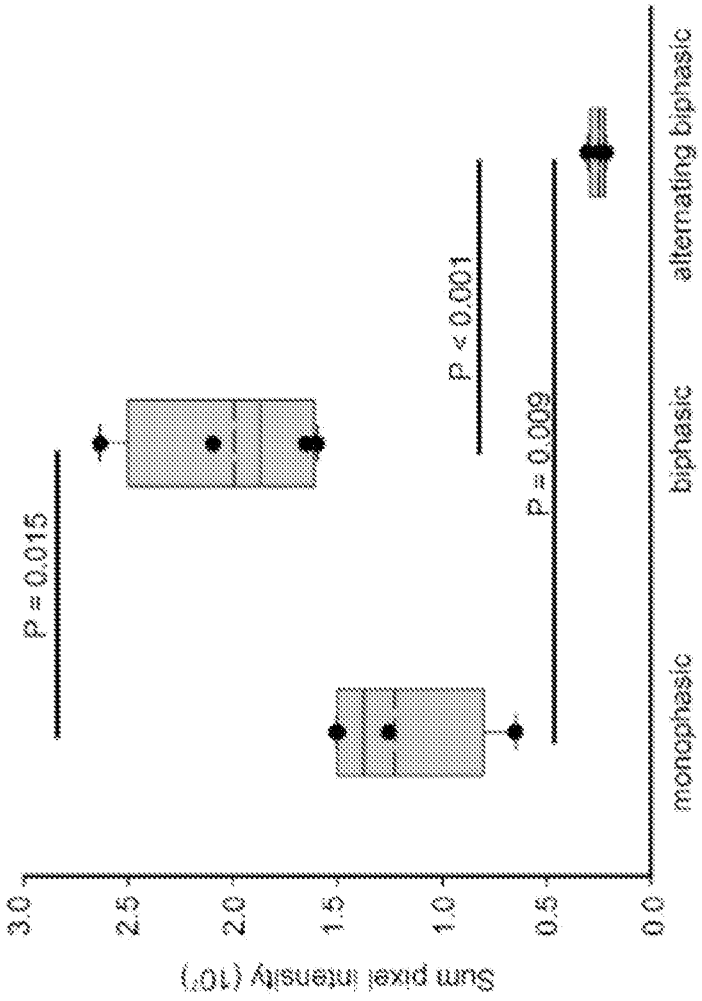
FIG. 4 shows One Way ANOVA, n=4 per treatment group for the results illustrated in FIG. 3, FIGS. 5*a*-5*d* show a mapped electric field and cell transformation results using a tandem array configuration.

FIG. 3 images 310, 330, 350 illustrate expression of reporter plasmid DNA by HEK293 cells using the same 2-electrode array driven using different pulse sequences. The Images of FIG. 3 are examples of mCherry fluorescence reporter expression in HEK293 cell monolayers following electrotransfer of naked plasmid DNA encoding the reporter under a cytomegalovirus (CMV) promoter; 10×100 μs pulses×10 mA in a pulse train delivered in monophasic mode using a prototype current stimulator developed by the inventors (a proprietary constant current stimulator, or a constant voltage stimulator may also be used) and a linear array of two contiguous elongate electrodes—where one is driven as an anode (+ve) and one is driven as a cathode (−ve). The stimulation sequences applied were applied in a monophasic mode 320—where all ten pulses had the same polarity, and in biphasic mode 340, where five pulses were the same polarity and then the second set of five pulses were of the opposite polarity (Biphasic). A third pulse train configuration had alternating positive and negative going pulses (alternating biphasic) 360. The interpulse interval was 400 μs. The DNA and the electrotransfer array was placed over the cells on a coverslip. The pulses were delivered and then the coverslip returned to culture for 48 hours prior to imaging. This example showed there was a significant improvement in DNA electrotransfer efficiency 330 in the biphasic mode 340. FIG. 4 shows One Way ANOVA, n=4 per treatment group.

The images in FIG. 3 show regions of DNA cell transfection by close field electrotransfer using a linear array electroporation probe, the electroporation occurring in a region adjacent the linear electrode array. The region in which the most cells are transfected being the region in which the electric field generated by the linear array is focused. The illustration of 310 shows cells transfected in response to application of a series of unipolar electroporation pulses 320 (referred to as a monophasic pulse sequence), in contrast 350 shows the cells transfected using the same electrode array driven using alternating polarity electroporation pulses (alternating biphasic), surprisingly, this charge-balanced alternating biphasic mode resulted in a pronounced reduction in DNA electrotransfer and reporter gene expression compared with the monophasic results 310. From the effect of DNA being driven to the side of the cells facing the negative electrode, one would expect alternating pulses to have an effect of driving DNA against both sides of the cells and improve transfection efficacy by the increase in cell area exposed to the DNA, surprisingly using alternating polarity provides very poor results.

Where the electrotransfer is performed using a sequence of several unipolar pulses and then a further sequence of several unipolar pulses of opposite polarity (referred to as biphasic), then the transfection efficacy is significantly improved as shown in 330 of FIG. 3. These results indicate that transfection efficacy is improved by prolonged driving the DNA toward the cells and sustain contact (adhesion) with the cell membrane for electrotransfer. This is evidenced by the monophasic results 310 compared with the alternating biphasic results 350 as shown in FIGS. 3 and 4. The further improvement in efficacy of the biphasic results provides evidence that following a prolonged period of electrotransfer driving DNA toward cells in one direction, changing to the opposite polarity and causing DNA to be driven toward the cells from the opposite direction and coat the opposite side further improves transfection efficacy.

The present disclosure describes a method for improving the efficiency of delivery of DNA into cells using a technique the inventors have called 'switch-mode electrotransfer'. This is a mode of electrotransfer using arrays of contiguous electrodes to generate electric fields having controlled electric field gradients adjacent the array. The switch mode operation uses a first sequence of unipolar pulses to generate a first shaped electric field with controlled electric filed gradients through a target region, and using a second sequence of unipolar pulses to generate a second shaped electric field, changing the direction of the electric field gradients through the treatment region. This change in electric field gradients causes molecules (DNA) to be driven toward the cells from a different direction and thereby coat a different area of the cell. Embodiments of the present system use of several unipolar pulses to generate and sustain each shaped electric field for a period sufficient to establish functional contact between the DNA molecules and cells to enable transfection. It should be noted that complete transfection or uptake of the DNA molecule by the cell may not occur during the application of the sequence of unipolar pulses. Establishing a functional contact should be understood to encompass any stage of uptake of the DNA by the cell that enables the uptake to progress despite the driving electrotransfer electric field ceasing or changing direction. This may include take up of DNA (or RNA) bound to the cell plasma membrane by processes such as endocytosis.

In FIG. 3 the inventors have provided proof of concept data showing enhanced expression of reporter plasmid DNA by HEK293 cells in a monolayer model using a continuous array of electrodes (in this example a linear array) when the polarity of electrodes in the gene electrotransfer array are switched during the pulse train. It is the nature of this switching which provides the improvement of DNA (or RNA) electrotransfer efficacy. The inventors show that switching polarity of pulses in accordance with specific requirements can achieve unanticipated improvement in DNA electrotransfer efficiency. In one embodiment of this method and system the train of electrotransfer pulses included a series of pulses of one polarity, followed by a series of pulses of opposite polarity. The inventors have shown that a potentially obvious and advantageous strategy of alternating between positive and negative polarity on electrodes (typically used for continuous electrical stimulation as a charge recovery strategy) is in fact counter-productive, resulting in lower efficiency of DNA electrotransfer. Thus, the unanticipated gain of efficiency by sequential building of DNA transfer using a series of unipolar current transfer pulses, followed by opposing polarity pulses provides the significant transfection efficacy advantages of this system.

The applicant's prior publication no WO2016/205895 discloses a system for controlling electric field gradients to, in turn, control regions where transfection occurs. The present development of this technology, disclosed herein, utilises this ability to shape electric fields to control electrotransfer coating of cells over a substantial area of the cells by changing the direction of the electric filed gradients. This essentially enables a controlled "painting" of the cells with DNA molecules for electrotransfer, by driving the molecules toward the cell from different directions. Further by using several unipolar pulses a functional contact can be formed between DNA molecules and cells before changing the direction of electric field gradients, and potentially driving DNA molecules away from the surface of the cells.

Figure 8A:
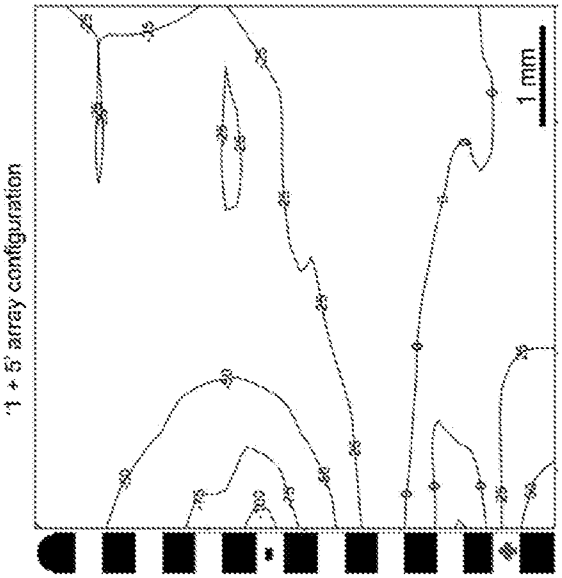
FIGS. 8*a*-8*b* show a mapped electric field and cell transformation results using a 1+5 array configuration.
Figure 8B:
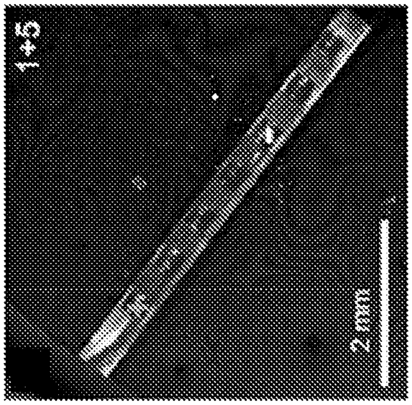
Figure 9B:
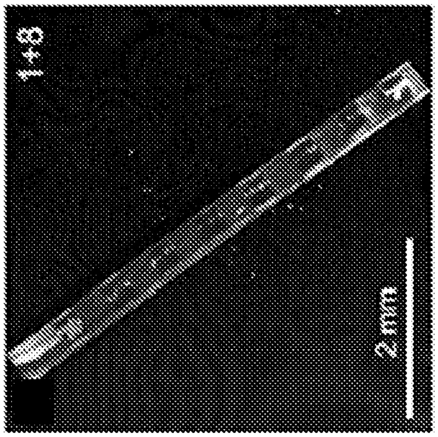
FIGS. 9*a*-9*b* show a mapped electric field and cell transformation results using a 1+8 array configuration.
Figure 9A:
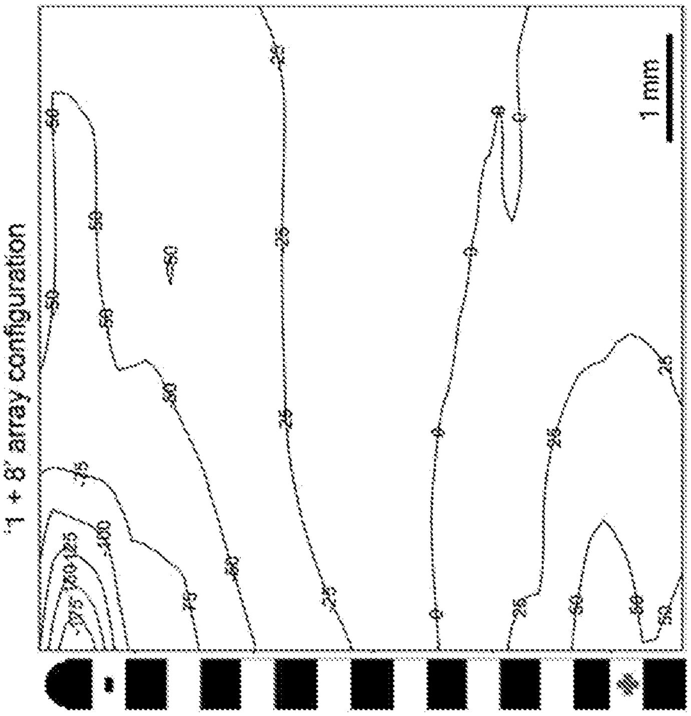

The electrotransfer technique of the present invention targets cells adjacent the array of electrodes, where the electric field is shaped around the array by the combination of current sources (anodes) and current returns (cathodes), gradients within the shaped electric field control the region where cell transfection occurs. By changing the direction of the electric field gradients coverage of cell by the treatment DNA molecules can be increased and subsequently improve transfection efficacy. Examples of mapped electric fields are shown in FIGS. 5-9 illustrating the variation in treatment regions based on changing array configuration and thereby the generated electric field. FIGS. 5*b*, 6*a*, 7*a*, 8*a* and 9*a* show examples of mapped electric field potentials resulting from different anode and cathode configurations for an eight electrode array and FIGS. 5*c*, 5*d*, 6*b*, 6*c*, 7*b*, 8*b* and 9*b* show resulting distributions of cell transformations after electroporation for each array configuration. The 8 electrodes within the array were configured as anodes and cathodes in the following combinations:

- Tandem—four juxtaposed cathodes then four juxtaposed anodes, all elements with 300 μm separation, total length 5 mm (illustrated in FIGS. 5*b-d*);
- Alternating—alternating cathodes and anodes within 300 μm separation, total length 5 mm (illustrated in FIGS. 6*a-c*);
- 1+2—a single anode and a single cathode within 300 μm separation (illustrated in FIGS. 7*a-b*);
- 1+5—a single anode and a single cathode with 2.45 mm separation (illustrated in FIGS. 8*a-b*); and
- 1+8—a single anode and a single cathode with 4.55 mm separation (illustrated in FIGS. 9*a-b*).

Figure 5A:
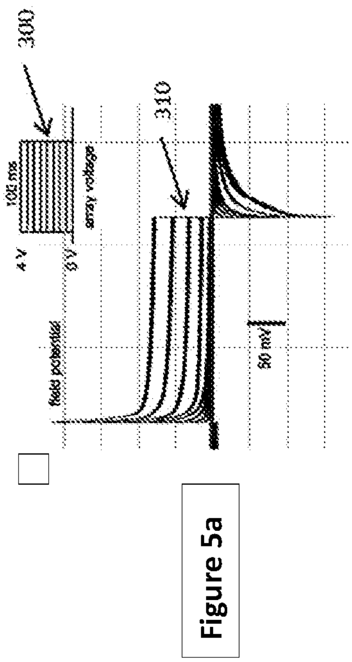
Figure 5B:
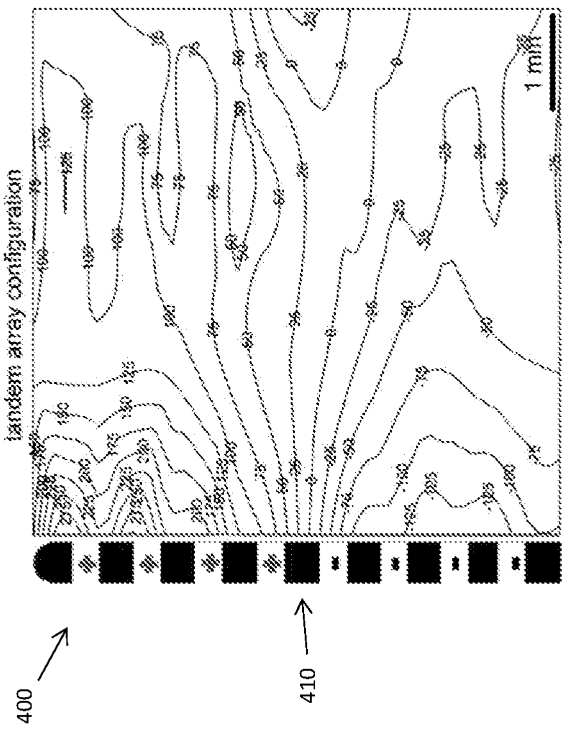
Figure 5C:
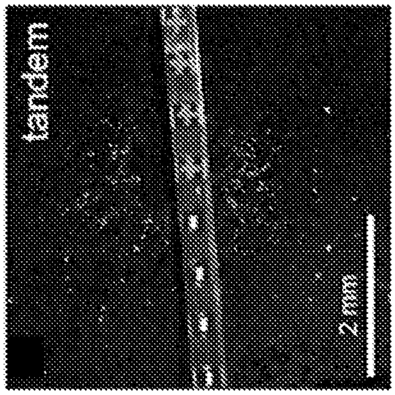
Figure 5D:
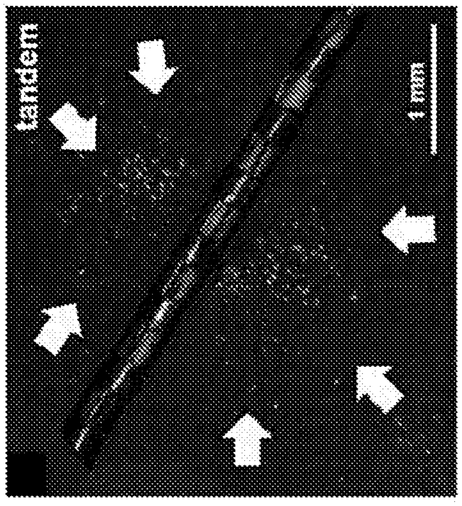
Figure 6B:
FIGS. 6*a*-6*c* show a mapped electric field and cell transformation results using an alternating array configuration.
Figure 6C:
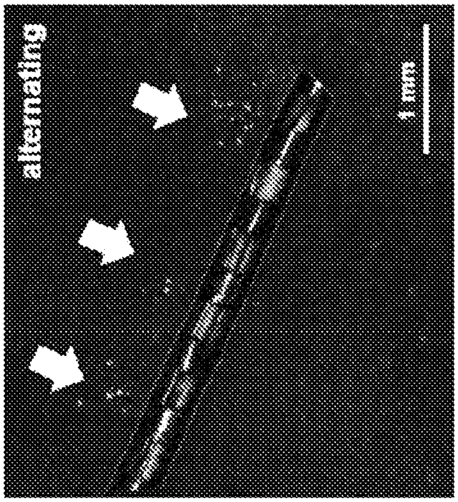
Figure 7B:
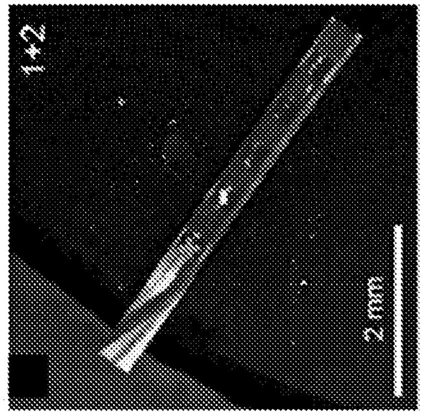
FIGS. 7*a*-7*b* show a mapped electric field and cell transformation results using a 1+2 array configuration.
Figure 7A:
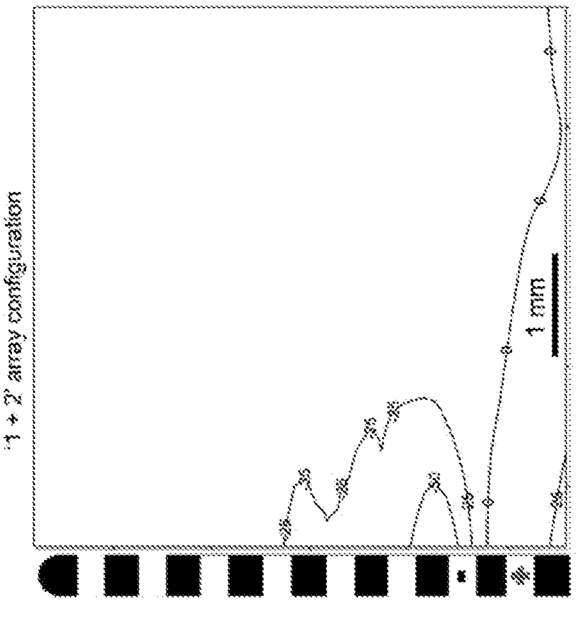

FIGS. 5*b*, 6*b*, 7*b*, 8*b* and 9*b*, show for comparison the effect of the array configuration on electroporation-mediated gene delivery, with all array configurations driven using a pulse sequence having the parameter set: 40V, 10 pulses, 50 ms duration, and 1 pulse/sec. Although all array configurations produced significant cell transductions, there was a significant effect on transformation efficiency due to array configuration, with variation in the space between anode and cathode, and in the number and pattern of anodes and cathodes. The 1+2 array driving configuration resulted in a spherical field of cells ~1 mm diameter, with the active electrodes at the centre (FIG. 7*b*). The alternating array driving configuration produced a linear bias to the field of transfected cells, extending the length of the array (~5 mm; 81.8±11.3 GFP-positive cells) as shown in FIGS. 6*b* and 6*c*. The 1+5 and 1+8 array driving configurations yielded smaller average numbers of transformed cells, which had a low-density distribution (FIGS. 8*b* & 9*b*). The transfection efficiency of the tandem configuration was significantly higher than any other configuration (FIGS. 5*c* and 5*d*) and the pattern was spherical in shape centred around the mid-point of the array, which was the confluence point between the four anodes and four cathodes. Testing by the inventors showed that the charge delivery required to achieve efficient cell transduction was least when the array was configured for anodes and cathodes ganged together as bipoles ('tandem' configuration).

Figure 6A:
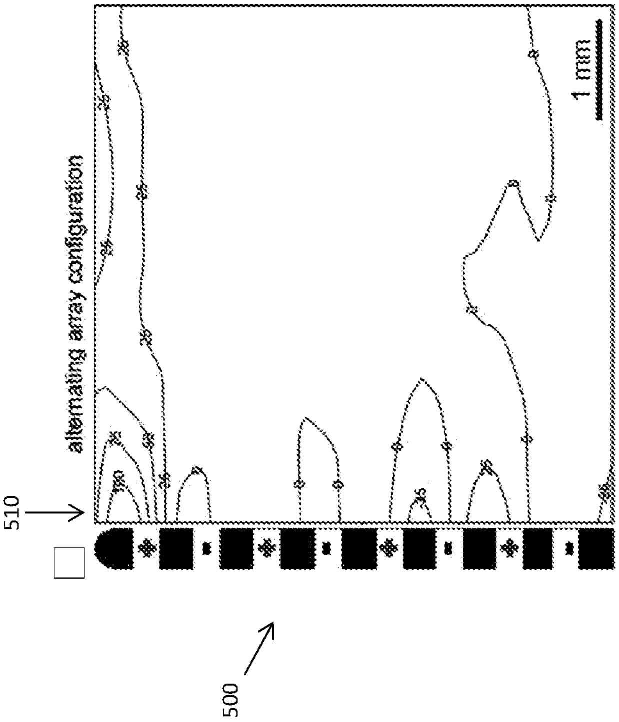

FIGS. 5*b*, 6*a*, 7*a*, 8*a* and 9*a*, show, for comparison, the electric field mapped for each array configuration, the field potentials were measured at the end of a 100 ms 4V pulse 300 applied to the array, shown in FIG. 5*a*. FIG. 5*a* also shows traces 310 of field potentials recorded with 0.5V steps up to 4V (100 ms duration) using the tandem array configuration. The 'tandem' configuration permitted significantly greater transduction efficiency compared with the equivalent number of electrodes wired in 'alternating' configuration. This study also demonstrated that smaller bipolar electrode configurations were less efficient (1+2, 1+5, 1+8). The reason that the 'tandem' array configuration shows unanticipated efficiency of cell transduction is attributed to the geometry of electric field focusing (FIG. 5*b*). The tandem array 400 exhibited the highest electric field contour density, with the null position tracking from the junction between the anodes and cathodes 410 (FIG. 5*b*). In contrast, despite utilising an equivalent number of electrodes, the alternating array configuration 500 had lower electric field density gradients, distributed along the array with the peak at the end of the array 510 (FIG. 6*a*). Given the spherical GFP positive field of cells centred around the null point of the 'tandem' array (FIGS. 5*c* and 5*d*; orthogonal to the point 410 between electrodes 4 & 5 in FIG. 5*b*), the data indicate that it is the electric field gradient across the cell, rather than the absolute step change in electric potential, drives electroporation and DNA uptake. The cell distributions for the other array configurations showed similar association with the measured electric field, and the drop off in number of GFP positive cells in the 1+2>1+5>1+8 was correlated with the broadening in the electric field relative to the electrodes.

The electric fields (and in particular gradients within the electric field) around the arrays were closely correlated with the spatial mapping of transformed cells. Thus, the cell transduction was dependent upon the electric potential gradient across the cell, rather than the absolute voltage. This is most evident with the contour map for the tandem configuration using 0.9% saline solution, where the null region in the field migrates orthogonally to the array between electrodes 4 and 5 (FIG. 5*b*). The field contour lines are steepest about this line and are maintained in a spherical shape which corresponds to the transduced cell maps. The magnitudes of the electric potential measurements are greatest at either end of the tandem array, but more uniform. As the distance separating the bipolar electrodes increased the field density declined, as evidenced by comparing results for the 1+2, 1+5 and 1+8 arrays in FIGS. 7*b*, 8*b*, and 9*b* respectively.

From the description above it should be apparent that combinations of electrode configuration and pulse parameters can be chosen to achieve a shaped electric filed having controlled electric field gradients. A key element for producing these controlled electric fields is the array configuration. An embodiment is envisaged of an array comprising a sheet of contiguous electrodes, for example arranged in two dimensional grid (i.e. rectangular, hexagonal, triangular etc. grid configuration) and connected to allow selective use of combinations of electrodes to effectively provide a variety of electrode configurations, and associated variations in electric filed shape and gradients when the selected electrodes are driven as anodes and cathodes. For example, a line of electrodes may be selected and driven with a first set of adjacent electrodes acting as a ganged cathode and another set of adjacent electrodes acting a ganged anode—a tandem configuration. And further set of aligned electrodes at an angle relative to the first line can then be selected and driven to change the direction of the electric field gradients. For example, selecting a different set of electrodes can cause an electric field to be generated through the target region with electric field gradients at an angle relative to the previous electric field. Where polarity is simply reversed the electric field with have similar shape with opposite electric field gradients. Selecting different sets of electrodes can alter the relative electric field gradient angle. Selecting different sets of electrodes can also alter the electric field shape. Any electrode configuration may be selected based on the target electric field shape (or shapes). Sequences of different electrodes may be selected and driven using electrotransfer pulses to optimally target the treatment region for delivery of charged molecules to cell surfaces via electric field gradients, shape and polarity.

Some embodiments extend this transfection targeting ability based on a linear array of electrodes to provide a "switch-mode" electrotransfer strategy, where both the polarity of pulses and the combination of electrodes transferring current within an array of electrodes can be switched within a pulse train, or multiple pulse trains, to rotate the focused electric field around the targeted cells within the tissue; effectively painting the DNA onto all surfaces of the cells; conceptually enabling 'vortex electrotransfer' DNA painting onto cells.

Figure 10:
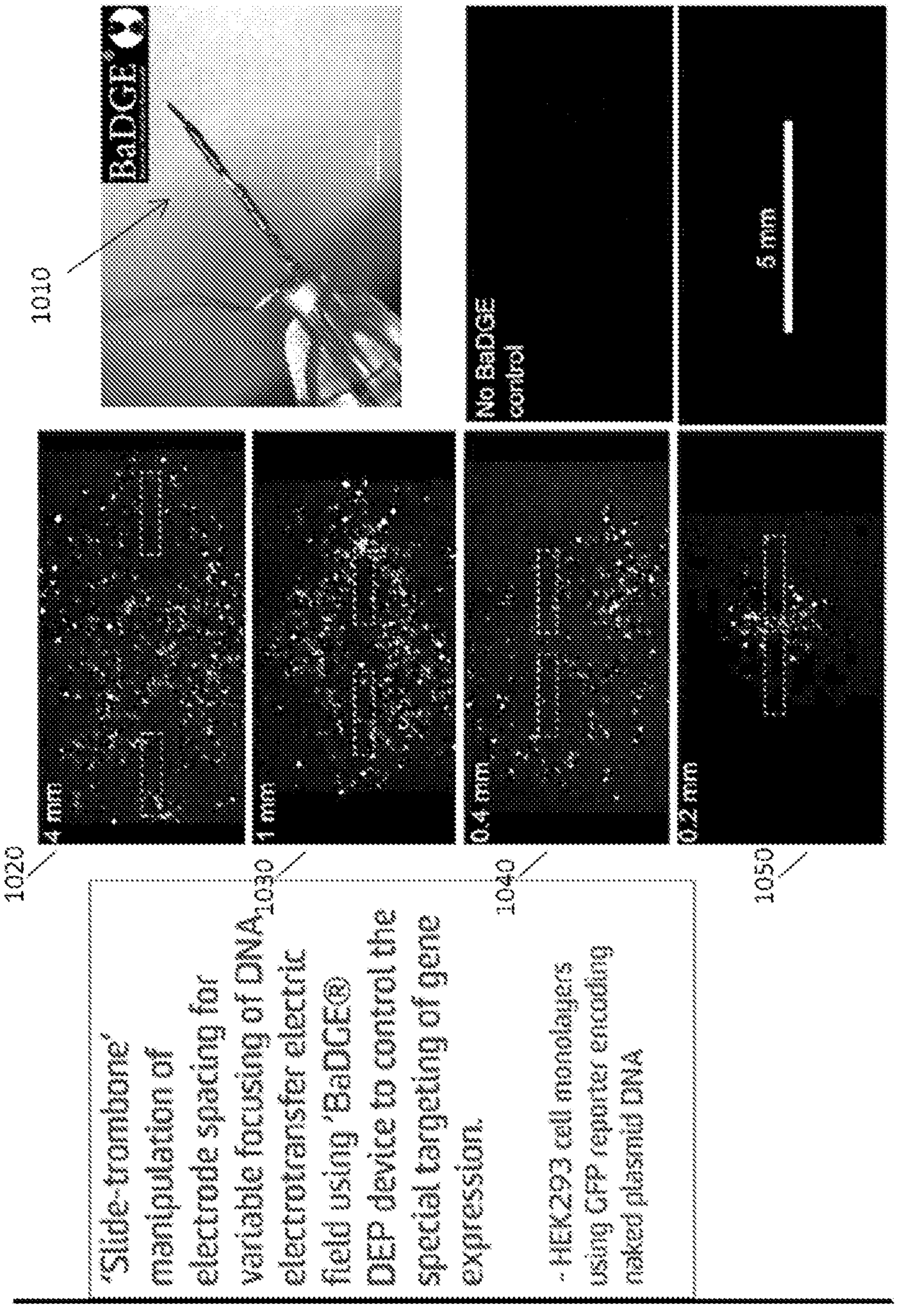
FIG. 10 illustrates some effects of manipulating the gap between anode and cathode.

In some embodiments the electrode configuration also controls the range of the transfection region relative to a linear electrode array. Looking at FIG. 5*b* the electric field gradient adjacent the middle of the array has the steepest electric field gradient, and the results of FIGS. 5*c* and 5*d* show that this region is where the most cells are transfected. The field shape is due to a combination of the linearly arranged elongate anode and cathode (in this configuration each of the anode and cathode comprising a plurality of adjacent linearly arranged electrodes). The elongate nature of the anode and cathode contribute to control of the generated electric field shape, and hence the transfection region. Altering the width of the gap between the elongate anode and cathode alters the range of the transfection area orthogonal to the array. By altering the gap, the electric field shape and hence the transfection area can be expanded or contracted. In the example shown, increasing the gap between the electrodes expands the electric filed and transfection area, whereas reducing the gap confined the field. It should be noted that this field shape control or vectoring is applicable for up to a gap of around 5 mm between electrodes for the pulse parameter used in this example. Increasing this gap may be feasible in conjunction with a corresponding increase in current levels, however due to potential negative side effects caused by higher current levels using further sets of electrodes may be preferable to enable treatment of a larger region. Controlling the radial spread of the electric field is also referred to as vectoring. FIG. 10 illustrates come effects of manipulating the gap between anode and cathode.

FIG. 10 images 1020 to 1050 illustrate the expansion and contraction of the transfection region with manipulation of the gap between the anode and cathode of the linear electrode array, in the examples of FIG. 10 probes of the type shown 1010 having linear, two electrode arrays with different spacing between the electrodes were used. The effect of manipulation of the electric field—achieved by decreasing the separation between two platinum-iridium electrodes (2 mm×0.35 mm diameter on an insulated scaffold—as shown in the upper right image) where a train of electric pulses (constant current, 100 μs×10 pulses, 400 μs pulse separation, 10 mA+ve phase). The data show the spatial control of electrotransfer of plasmid DNA (a Green fluorescent reporter protein—GFP—under a cytomegalovirus (CMV) promoter) delivered to monolayers of Human Embryonic Kidney (HEK) 293 cells, using an isotonic polysaccharose carrier. The DNA and the electrotransfer array was placed over the cells on a coverslip. The pulses were delivered and then the coverslip returned to culture for 48 hours prior to imaging. The highest electric field strength is around the null point between the two electrodes. As the electrodes separate, the electric field sufficient for DNA electrotransfer expands, until an optimum dispersion and cell density of expression of the recombinant DNA expression cassette is obtained (between 1-4 mm electrode separation).

In further embodiments manipulation of the pulse polarity can be combined with dynamic alteration of the shape of the electric field by switching between electrodes within the close field electrode array (for example expanding or contracting the electric field). This switching may occur during a pulse train sequence, or between pulse trains so that both the polarity and vectoring of the field are rotated around the target cells. This serves to 'paint' the DNA onto the cell surface membrane. A means for altered vectoring of the electric field can be seen by the effect of shifting the separation of two primary electrodes, each 2 mm length and 350 μm diameter, along a linear array—as shown in FIG. 10.

Figure 11:
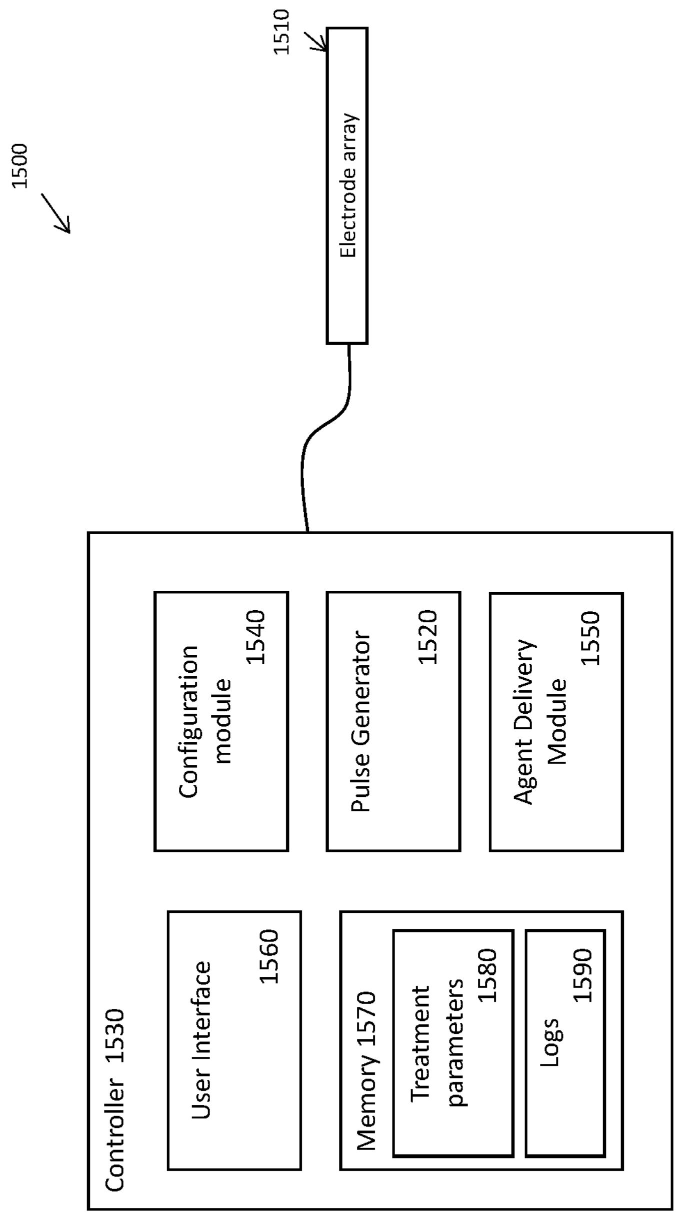
FIG. 11 is a block diagram of an alternative system configuration.

System embodiments may use individual components for the array, pulse generator and controller, or these functions may be integrated into a consolidated system. A block diagram of a system embodiment including a controller is shown in FIG. 11, the system 1500 comprises the electrode array 1510 as described above and a controller 1530. In this block diagram the controller is shown including the pulse generator 1520 however the pulse generator may be a separate piece of equipment. The illustrated embodiment also includes optional features such as a configuration module 1540 to enable control of the array configuration as discussed above; an agent delivery module 1550 to control delivery of the therapeutic agent via the probe; a user interface 1560; and memory 1570 for storing data such as treatment parameters 1580 and treatment logs 1590.

In an embodiment the controller is implemented using a computer system which may comprise the full functionality of the system, or control dedicated hardware components via data connections. Any possible configuration of controller hardware, firmware and software is envisaged within the scope of the invention. In an embodiment the controller functionality may be implemented using a dedicated hardware device, for example a version of a pulse generator modified to provide controller functionality or dedicated hardware device say including hardware logic ASIC (application specific integrated circuit) or FPGA (field programmable gate array), firmware and software implementing the controller functionality. An advantage of a dedicated system can be independence from commercial software platforms and operating systems, this may be advantageous in obtaining regulatory approval and constraining use of the system to the intended purpose. However, a disadvantage of this embodiment may be increased system development and ongoing maintenance costs, and lack of flexibility to take advantage of new technologies or developments in the technical field.

Alternatively, the controller functionality may be provided as a software program executable on a computer system, such as a personal computer, server or tablet, and configured to provide control instructions to an independent pulse generator and other optional hardware such as an agent delivery actuator. A software-based controller embodiment executable using commercially available computer hardware is envisaged to provide a specialist with a user interface 1560 to input parameters for the electroporation treatment 1580 that are then stored in memory 1570 for use to drive the pulse generator 1520 and optionally configuration module 1540 and agent delivery module during electroporation treatment delivery 1550. In an embodiment this may comprise the controller analysing a target treatment region parameters and carrier solution parameters; determining appropriate electrode array configuration(s); and defining at least one sequence of pulses calculated based on the relationships discussed above to achieve the target treatment field for each appropriate array configuration. In embodiments where agent delivery is controllable by the controller the controller may also calculate and define agent delivery actuation in the treatment pulse sequence. In embodiments where the array configuration is controllable by the controller the controller also defines the array configuration for implementation by the configuration module. In embodiments where the array configuration is dependent upon selection of fixed array configurations, either a selected probe array configuration may be input to the controller by the specialist/surgeon/clinician or the controller may output probe selection recommendations. If more than one combination of array and pulse sequence is determined to be appropriate to satisfy the treatment requirements the possible combinations may be output to the surgeon/specialist/clinician for selection.

Some embodiments of the controller may provide software to model the treatment. In some embodiments data utilised for modelling may include patient imaging data (i.e. MRI or CT scans) to enable modelled treatment fields to be considered in conjunction with patient data. Modelling data can also include options for therapeutic agent carrier solutions. For example, to determine viable or optimal carrier solution parameters to safely achieve desired treatment outcomes via modelling. Alternatively, where a limited number of carrier solution options are available, to model potential outcomes for each option to facilitate decision making by the specialist/surgeon/clinician.

It should be appreciated that system functionality provided associated with planning treatment may be complex and utilise sophisticated software models to determine the required data to drive the physical treatment apparatus. But the actual data required to physically execute the treatment can be quite simple—a defined array configuration (which may even be a fixed array), a sequence of timed pulses and optionally signals for controlling agent delivery for the chosen agent solution. Thus, the controller may simply output the sequence data for driving the physical treatment equipment.

Embodiments of the pulse generator 1520 can operate under voltage or current-driven modes. In an embodiment the pulse generator is a stand-alone independent unit having its own power supply independent of the controller. The pulse generator may be in data communication with the controller to enable the controller to program the pulse generator with the pulse sequence. Alternatively, the pulse sequence may be calculated by the controller and loaded into the pulse generator by manual programming or data transfer (for example by direct connection, wireless connection or via physical media such as a portable solid state memory device) and the pulse generator operated independently of the controller for therapy delivery. Isolation of the pulse generator from the controller may be a safety requirement for some systems, in particular enabling the disposable DNA (or RNA) delivery probes to be operated using pulse generators already approved and available for human clinical use. In some countries this may enable independent regulatory approval of the probes for use in conjunction with a selection of commercially available and regulatory approved pulse generators.

Embodiments of the present system and method may be advantageously applied in the fields of DNA therapeutics, molecular therapies involving electrotransfer of nucleic acids, such as naked plasmid DNA and RNA, or other charged molecules. Embodiments can be utilised in Pharmaceutical and Biotech industries, and can be applicable for any industry engaged in DNA-based therapies and wanting an efficient non-viral DNA delivery platform.

Figure 12A:
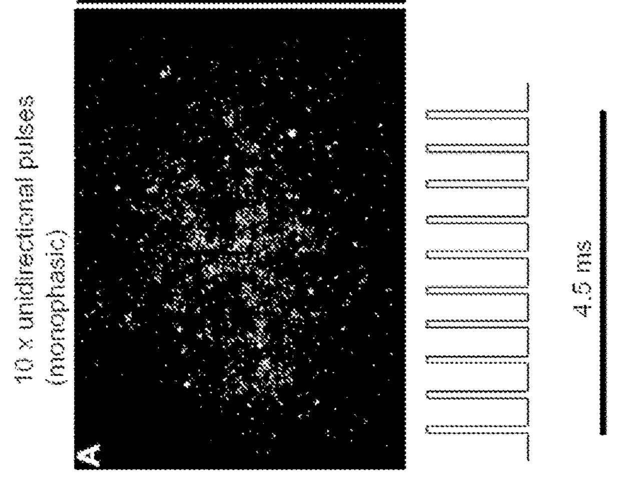
FIG. 12*a-c* show a first example of comparative analysis of monophasic and biphasic electrotransfer using an 8-electrode linear array.
Figure 12B:
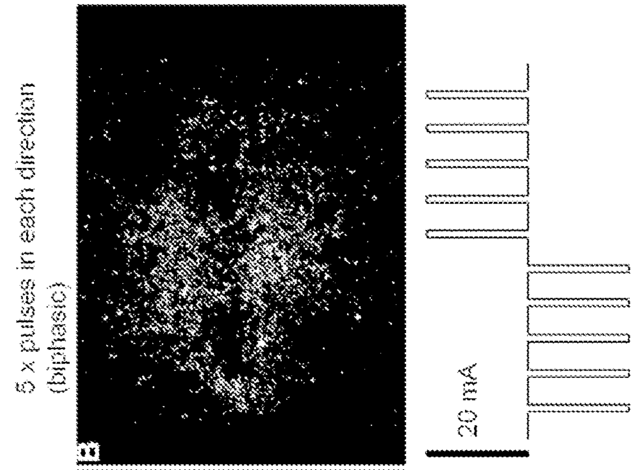
Figure 12C:
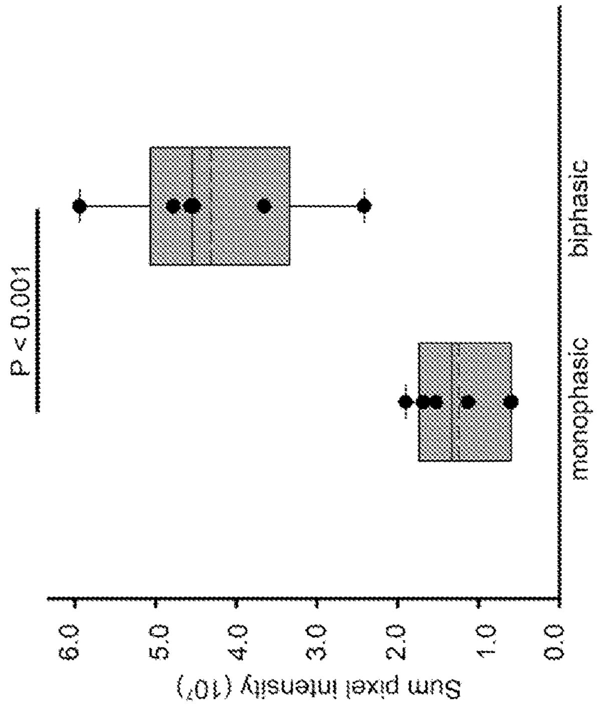
Figure 13:
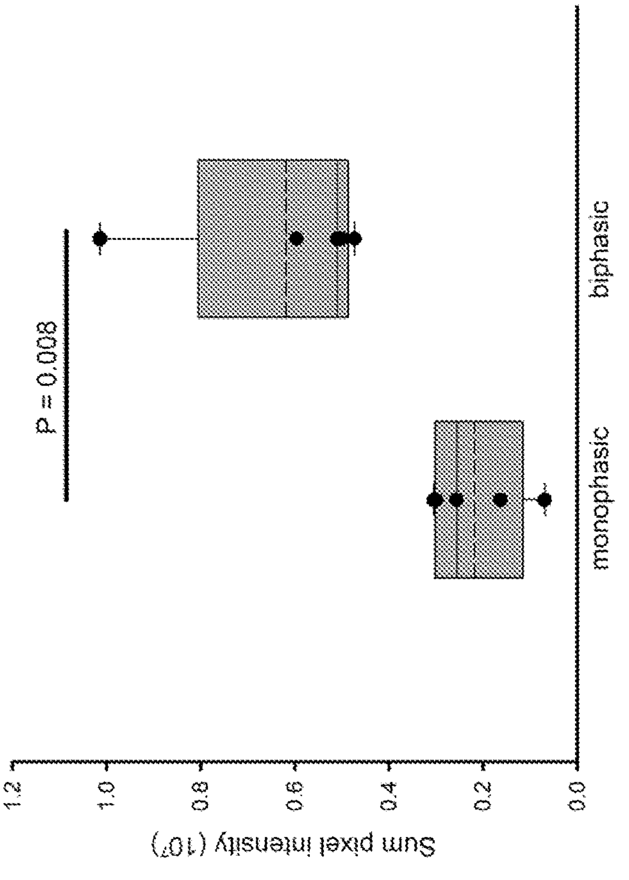
FIG. 13 shows a second example of comparative analysis of monophasic and biphasic electrotransfer using an 8-electrode linear array.
Figure 14:
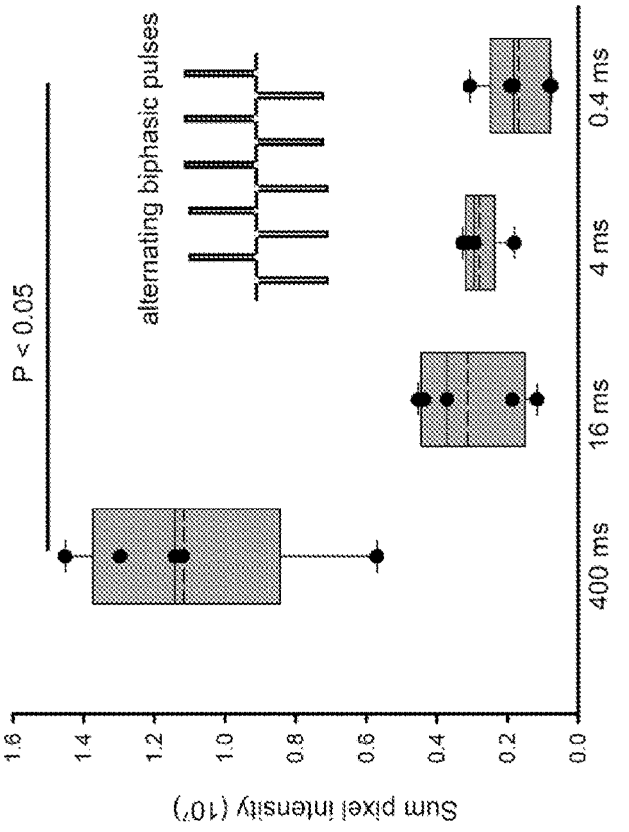
FIG. 14 is a graph illustrating that extending the inter-pulse interval with alternating biphasic pulses enhances gene expression.

FIGS. 12-14 show examples of prototype test results.

Example 1: Effect of Electric Pulse Polarity on Fluorescent Reporter Protein Expression Following Bionic Array-Directed Gene Electrotransfer (BaDGE) of mCherry Reporter Plasmid at 1 μg/μl Concentration—Monophasic Versus Biphasic Pulse Trains FIG. 12*a-c* show results for a comparative example of electrotransfer using a pulse sequence of unidirectional pulses of one polarity only (FIG. 12*a*) and a biphasic pulse sequence having the same number of pulses and amplitude but with a change in polarity (FIG. 12*b*). The test results in FIG. 12 illustrate the effect of switching electrode polarity on mCherry expression in HEK293 cells. The mCherry fluorescence was imaged using a confocal microscope, 4 days after electrotransfer using an 8-electrode animal model cochlear implant array for the DNA electrotransfer. The array was wired in a tandem configuration (four adjacent Pt/Ir electrode bands ganged as anodes and the next four electrodes ganged as cathodes). Round coverslips (18 mm diameter) were seeded ~24 hrs prior to electrotransfer, at which time the HEK293 cells were around 50% confluent. Electrotransfer was performed using 10×40 mA 100 μs pulses delivered via the gene delivery array after 20 μl DNA was delivered (1 ug/ul each CMVp-mCherry and pFAR4-BDNF-NT3) in 9% sucrose, 0.09% NaCl & 500 uM NaOH. Electrotransfer transfected coverslips were then placed into 30 mm petri dishes with 4 ml of Dulbecco's Modified Eagle's Medium (DMEM) cell culture media containing 5% Fetal Bovine Serum (FBS). Monophasic refers to 5 pulses of a fixed polarity. Biphasic refers to 5 pulses applied with the electrodes in one polarity, then 5 pulses with the polarity reversed. After 4 days live cells were imaged and subsequently 2×0.5 ml aliquots of media were snap frozen for BDNF and NT-3 ELISA. FIG. 12*a* shows an example of a coverslip transfected with 10 pulses, each pulse with the same 4 ganged electrodes active and opposite 4 as return. FIG. 12 *b* shown an example of a coverslip transfected with 5 pulses with the same 4 ganged electrodes active and opposite 4 as return, followed by 5 pulses after switching electrode polarity. FIG. 12*c* shows boxplots with data from each coverslip overlaid, boundaries represent 25% and 75% data limits, bars represent 95% distribution limits. Solid centre line is the median, dashed line is the mean. Statistical comparison by t-test.

Example 2: Effect of Electric Pulse Polarity on Fluorescent Reporter Protein Expression Following Bionic Array-Directed Gene Electrotransfer (BaDGE) of mCherry Reporter Plasmid at 4 μg/μl Concentration—Monophasic Versus Biphasic Pulse Trains FIG. 13 shows an example of the effect of switching electrode polarity on nuclear localized mCherry reporter expression in HEK293 cells. The mCherry fluorescence was imaged by confocal microscope 4 days after electrotransfer using an 8-electrode animal model cochlear implant array for the DNA electrotransfer. The bionic array was wired in a tandem configuration (four adjacent Pt/Ir electrode bands ganged as anodes and the next four electrodes ganged as cathodes). Round coverslips (18 mm diameter) were seeded with HEK293 cells ~24 hrs prior to BaDGE at which time the HEK293 cells were around 50% confluent. BaDGE was performed using 10×40 mA 100 μs pulses delivered via the gene delivery array after 20 ul DNA was applied to the coverslip (4 ug/ul CMVp-mCherry) in a carrier solution of 9% sucrose, 0.09% NaCl & 500 μM NaOH (total plasmid DNA concentration 4 μg/μl). Electrotransfer transfected coverslips were then placed into 30 mm petri dishes with 4 ml of Dulbecco's Modified Eagle's Medium (DMEM) cell culture media containing 5% Fetal Bovine Serum (FBS). Monophasic refers to all 10 pulses of a fixed electrode polarity. Biphasic refers to 5 pulses applied with the electrodes in one polarity, then 5 pulses with the polarity reversed. Boxplots with data from each coverslip overlaid. Boundaries represent 25% and 75% data limits, Bars represent 95% distribution limits. Solid centre line is the median; dashed line is the mean. Statistical comparison by Mann-Whitney Rank Sum Test.

Example 3: Effect of Inter-Pulse Interval with Alternating Polarity—Driven Fluorescent Reporter Protein Expression Following Bionic Array-Directed Gene Electrotransfer (BaDGE) of mCherry Reporter Plasmid FIG. 14 shows a graph of results illustrating that extending the inter-pulse interval with alternating biphasic pulses enhances gene expression. This test used alternating biphasic polarity of BaDGE electrodes (changing from (+) to (−) between each pulse; 10×4 ms duration) results in increased transfection of HEK293 cells when the inter-pulse interval exceeds 16 ms; 2 μg/μl CMVp-mCherry reporter plasmid in a carrier solution of 9% sucrose, 0.09% NaCl & 500 μM NaOH (20 μl total volume plasmid DNA applied to the HEK293 cells on an 18 mm coverslip). n=5 each condition; sum pixel intensity across the coverslip, represents the integration of the mCherry-derived flurorescence (nuclear localized) by confocal imaging. Kruskal-Wallis one-way ANOVA on ranks with Tukey-test multiple pairwise comparisons.

It will be understood to persons skilled in the art of the invention that many modifications may be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

The invention claimed is:

1. A method of controlling electrotransfer delivery of therapeutic molecules to targeted groups of cells using a system comprising an array of two or more physically contiguous electrodes configured to be inserted into biological tissue and a pulse generator configured to selectively drive the two or more physically contiguous electrodes as one or more anodes and one or more cathodes for application of one or more electrical pulses, the method comprising:

determining a first selection of the two or more physically contiguous electrodes to drive as the one or more anodes and the one or more cathodes using one or more electric pulses, and, for the first selection of the two or more physically contiguous electrodes, determining electrical pulse parameters for the one or more electric pulses to generate a first shaped electric field for a target treatment region adjacent the array, wherein a physical configuration of the two or more physically contiguous electrodes, the first selection of the two or more physically contiguous electrodes as anodes and cathodes, and the electrical pulse parameters, control contours of gradients within the first shaped electric field for the target treatment region adjacent the array;

determining a second selection of the two or more physically contiguous electrodes to drive as the one or more anodes and the one or more cathodes using one or more electric pulses, and, for the second selection of the two or more physically contiguous electrodes, determining electrical pulse parameters for the one or more electric pulses to generate a second shaped electric field for the target treatment region adjacent the array;

determining a duration of a waiting period between generating the first shaped electric field and generating the second shaped electric field;

controlling the pulse generator to apply a first sequence of a plurality of unipolar pulses using the first selection of electrodes driven as the one or more anodes and the one or more cathodes to generate the first shaped electric field; and after the determined waiting period, controlling the pulse generator to apply a second sequence of a plurality of unipolar pulses using the second selection of electrodes driven as the one or more anodes and the one or more cathodes to provide the second shaped electric field, wherein a direction of the second shaped electric field is different from a direction of the first shaped electric field and a polarity of the plurality of unipolar pulses of the second sequence is opposite to a polarity of the plurality of unipolar pulses of the first sequence.

2. A method as claimed in claim 1, wherein the first selection of the two or more physically contiguous electrodes comprises a linear configuration of one or more anodes and one or more cathodes, and the second selection of the two or more physically contiguous electrodes comprises the first selection of the two or more physically contiguous electrodes with the one or more anodes and the one or more cathodes switched to thereby reverse polarity.

3. A method as claimed in claim 1, wherein the array is a two-dimensional array and wherein the first selection of the two or more physically contiguous electrodes comprises a configuration of the one or more anodes and the one or more cathodes, and the second selection of the two or more physically contiguous electrodes comprises a configuration of electrodes including different electrodes from the first selection, selected to generate a change in electric field gradients within the target treatment region.

4. A method as claimed in claim 1, further comprising the steps of determining one or more further selections of the two or more physically contiguous electrodes to drive as the one or more anodes and the one or more cathodes using the one or more electric pulses, and, for the one or more further selections of the two or more physically contiguous electrodes, determining electrical pulse parameters for the one or more electric pulses to generate a further shaped electric field for the target treatment region adjacent the array; and for each of the one or more further selections of the two or more physically contiguous electrodes, controlling the pulse generator to apply a further sequence of one or more unipolar pulses using each of the one or more further selections of the two or more physically contiguous electrodes driven as the one or more anodes and the one or more cathodes to generate each further shaped electric field, wherein each of the one more further selections generates different controlled electric field gradients within the target treatment region compared to controlled electric field gradients of a preceding electric field.

5. A method as claimed in claim 4 wherein a sequence of said each of the one or more further selections the two or more physically contiguous of electrodes and the electrical pulses is chosen to generate a sequence of electric fields where subsequent electric fields each have an electric field gradient through the target treatment region at an incremental angle relative to a preceding electric field.

6. A method as claimed in claim 1 wherein increasing or decreasing spacing between the one or more anodes and the one or more cathodes is used to control a radius of the target treatment region.

7. A method as claimed in claim 1, wherein a direction of the gradients within the second shaped electric field is different from a direction of the gradients within the first shaped electric field.

8. A method as claimed in claim 1, wherein the waiting period duration is at least 10 ms.

9. A method as claimed in claim 8, wherein the waiting period duration is less than 6000 ms.

10. A method of controlling an electrotransfer delivery system, the electrotransfer delivery system comprising an array of two or more physically contiguous electrodes configured to be inserted into biological tissue and a pulse generator configured to selectively drive the two or more physically contiguous electrodes as one or more anodes and one or more cathodes for application of one or more electrical pulses to produce electric fields adjacent the array, the method comprising:

determining a first selection of the two or more physically contiguous electrodes to drive as the one or more anodes and the one or more cathodes using one or more electric pulses, and, for the first selection of the two or more physically contiguous electrodes, determining electrical pulse parameters for the one or more electric pulses to generate a first shaped electric field for a target treatment region adjacent the array, wherein a physical configuration of the two or more physically contiguous electrodes, the first selection of the two or more physically contiguous electrodes as anodes and cathodes, and the electrical pulse parameters, control contours of gradients within the first shaped electric field for the target treatment region adjacent the array;

determining a second selection of the two more physically contiguous electrodes to drive as the one or more anodes and the one or more cathodes using one or more electric pulses, and, for the second selection of the two or more physically contiguous electrodes, determining electrical pulse parameters for the one or more electric pulses to generate a second shaped electric field for the target treatment region adjacent the array;

determining a duration of a waiting period between generating the first shaped electric field and generating the second shaped electric field;

controlling the pulse generator to apply a first sequence of a plurality of unipolar pulses using the first selection of electrodes driven as the one or more anodes and the one or more cathodes to generate the first shaped electric field; and after the determined waiting period, controlling the pulse generator to apply a second sequence of a plurality of unipolar pulses using the second selection of electrodes driven as the one or more anodes and the one or more cathodes to provide the second shaped electric field, wherein a direction of the second shaped electric field is different from a direction of the first shaped electric field and a polarity of the plurality of unipolar pulses of the second sequence is opposite to a polarity of the plurality of unipolar pulses of the first sequence.

11. A method as claimed in claim 10 wherein the waiting period duration is at least 10 ms.

12. A method as claimed in claim 11, wherein the first selection of the two or more physically contiguous electrodes comprises a linear configuration of one or more anodes and one or more cathodes, and the second selection of the two or more physically contiguous electrodes comprises the first selection of the two or more physically contiguous electrodes with the one or more anodes and the one or more cathodes switched to thereby reverse polarity.

13. A method as claimed in claim 11, wherein the array is a two-dimensional array and wherein the first selection of the two or more physically contiguous electrodes comprises a configuration of the one or more anodes and the one or more cathodes, and the second selection of the two or more physically contiguous electrodes comprises a configuration of electrodes including different electrodes from the first selection, selected to generate a change in electric field gradients within the target treatment region.

14. A method as claimed in claim 10, wherein the first selection of the two or more physically contiguous electrodes comprises a linear configuration of one or more anodes and one or more cathodes, and the second selection of the two or more physically contiguous electrodes comprises the first selection of the two or more physically contiguous electrodes with the one or more anodes and the one or more cathodes switched to thereby reverse polarity.

15. A method as claimed in claim 10, wherein the array is a two-dimensional array and wherein the first selection of the two or more physically contiguous electrodes comprises a configuration of the one or more anodes and the one or more cathodes, and the second selection of the two or more physically contiguous electrodes comprises a configuration of electrodes including different electrodes from the first selection, selected to generate a change in electric field gradients within the target treatment region.

16. A method as claimed in claim 10, further comprising the steps of:

determining one or more further selections of the two or more physically contiguous electrodes to drive as the one or more anodes and the one or more cathodes using the one or more electric pulses, and, for the one or more further selections of the two or more physically contiguous electrodes, determining electrical pulse parameters for the one or more electric pulses to generate a further shaped electric field for the target treatment region adjacent the array; and for each of the one or more further selections of the two or more physically contiguous electrodes, controlling the pulse generator to apply a further sequence of one or more unipolar pulses using each of the one or more further selections of the two or more physically contiguous electrodes driven as the one or more anodes and the one or more cathodes to generate each further shaped electric field, wherein each of the one or more further selection generates different controlled electric field gradients within the target treatment region compared to controlled electric field gradients of a preceding electric field.

17. A method as claimed in claim 16, wherein a sequence of said each of the one or more further selections of the two or more physically contiguous electrodes and the electrical pulses is chosen to generate a sequence of electric fields where subsequent electric fields each have electric field gradients through the target treatment region at an incremental angle relative to a preceding electric field.

18. A method as claimed in claim 10, wherein increasing or decreasing spacing between the one or more anodes and the one or more cathodes is used to control a radius of the target treatment region.

19. A method as claimed in claim 10, wherein a direction of the gradients within the second shaped electric field is different from a direction of the gradients within the first shaped electric field.

* * * * *